US010047162B2

(12) United States Patent
Kettenberger et al.

(10) Patent No.: US 10,047,162 B2
(45) Date of Patent: Aug. 14, 2018

(54) SEQUENCE DEPENDENT AGGREGATION

(71) Applicant: Hoffmann-La Roche Inc., Little Falls, NJ (US)

(72) Inventors: Hubert Kettenberger, Munich (DE); Stefan Klostermann, Neuried (DE); Ulrich Kohnert, Habach (DE); Sebastian Neumann, Weilheim (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/832,505

(22) Filed: Aug. 21, 2015

(65) Prior Publication Data

US 2016/0068602 A1    Mar. 10, 2016

Related U.S. Application Data

(62) Division of application No. 13/515,428, filed as application No. PCT/EP2010/070063 on Dec. 17, 2010, now Pat. No. 9,150,641.

(30) Foreign Application Priority Data

Dec. 22, 2009   (EP) .................................... 09015832

(51) Int. Cl.
C07K 16/00      (2006.01)
C07K 16/28      (2006.01)
C07K 16/46      (2006.01)

(52) U.S. Cl.
CPC .......... C07K 16/2866 (2013.01); C07K 16/00 (2013.01); C07K 16/2875 (2013.01); C07K 16/461 (2013.01); C07K 2317/24 (2013.01); C07K 2317/567 (2013.01)

(58) Field of Classification Search
CPC .. C07K 16/00; C07K 16/461; C07K 2317/24; C07K 2317/567
USPC .................... 424/133.1; 530/387.3
See application file for complete search history.

(56) References Cited

U.S. PATENT DOCUMENTS

| | | | |
|---|---|---|---|
| 5,202,238 A | 4/1993 | Fell et al. | |
| 5,204,244 A | 4/1993 | Fell et al. | |
| 9,150,641 B2 * | 10/2015 | Kettenberger | C07K 16/00 |
| 2009/0104187 A1 * | 4/2009 | Kovacevich | C07K 16/241 424/133.1 |
| 2009/0238825 A1 * | 9/2009 | Kovacevich | C07K 16/241 424/133.1 |
| 2016/0159928 A1 * | 6/2016 | Bazirgan | C07K 16/00 506/17 |
| 2016/0168231 A1 * | 6/2016 | De Los Rios | C07K 16/00 506/17 |

FOREIGN PATENT DOCUMENTS

| | | |
|---|---|---|
| EP | 0 307 434 B2 | 9/1988 |
| EP | 1 291 360 A1 | 12/2003 |
| EP | 2 050 765 A1 | 6/2012 |
| WO | 98/08097 | 2/1998 |
| WO | 98/52976 A1 | 11/1998 |
| WO | 03/002607 A1 | 1/2003 |
| WO | 2004/020579 A2 | 3/2004 |
| WO | 2006/029879 A2 | 3/2006 |
| WO | 2006/050491 A2 | 5/2006 |
| WO | 2006/055778 A2 | 6/2006 |
| WO | 2006/072564 A1 | 7/2006 |
| WO | 2006/096653 A2 | 9/2006 |
| WO | 2009/000098 A2 | 12/2008 |
| WO | 2009/000098 A3 | 12/2008 |

OTHER PUBLICATIONS

*Abbboe Deutschland GmbH & co.*, vs *Janssen Biotech, Inc.*, CAFC 2013-1338, 1346 (Jul. 1, 2014).
Chiti et al., "Kinetic partitioning of protein folding and aggregation" Nature Structural Biol 9(2):137-143 (Feb. 2002).
Chiti, F., "Relative importance of hydrophobicity, net charge, and secondary structure propensities in protein aggregation" Protein Reviews (ed. By Uversky and Fink (Springer)), 4 Chapter 3:43-59 (2006).
Chowdhury et al., "Engineering scFvs for improved stability" Methods Molec Biol 207:237-254, Coleman.
"Effects of amino acid sequence changes on antibody-antigen interactions" Res Immunol 145:33-36 (1994).
De Pascalis et al., "Grafting of 'abbreviated' complementarity-determining regions containing specifiicity-determining residues essential for ligand contact to engineer a less immuogenic humanized monoclonal antibody" J Immunol 169:3076-3084 (2002).
Dufner et al., "Harnessing phage and ribosome display for antibody optimisation" Trends Biotechnol 24(11):523-529 (2006).
Dynamic Light Scattering: Application of Photon Correlation Spectroscopy Pecora, R.,Plenum Press, (1985).
Edelman et al., "The covalent structure of an entire γG immunoglobulin molecule" P Natl Acad Sci USA 63:78-85 (1969).
Honegger et al., "The influence of the framework core residues on the biophysical properties of immunoglobulin heavy chain variable domains" Protein Eng Des Sel 22(3):121-134 (Jan. 10, 2009).
Kabat et al. Sequence of Proteins of Immunological Interest Fifth edition,NIH Publication,:91-3242 (1991).

(Continued)

*Primary Examiner* — Lynn A Bristol
(74) *Attorney, Agent, or Firm* — Jennifer L. Davis

(57) ABSTRACT

Herein is reported a method for reducing the aggregation of an immunoglobulin in solution comprising the steps of i) comparing the amino acid sequence of the fourth framework region of the heavy chain of an antibody with a reference or germline sequence and determining whether one or more threonine residues and/or serine residues have been replaced by a different amino acid residue, and ii) modifying the amino acid sequence of the immunoglobulin by reverting the exchanged threonine residues and/or serine residues back to threonine or serine of the reference or germline sequence and thereby reducing the aggregation of an immunoglobulin in solution.

5 Claims, 6 Drawing Sheets

(56) References Cited

OTHER PUBLICATIONS

Kuegler et al., "Stabilization and humanization of a single-chain Fv antibody fragment specific for human lymphocyte antigen CD19 by designed point mutations and CDR-grafting onto a human framework" Protein Eng Des Sel 22(3):135-147 (Feb. 1, 2009).

Kyte et al., "A simple method for displaying the hydropathic character of a protein" J Mol Biol 157:105-132 (1982).

Lund et al., "Oligosaccharide-protein interactions in IgG can modulate recognition by Fc gamma receptors" FASEB J. 9(1):115-9 (1995).

Measurement of Suspended Particles by Quasielectric Light Scattering Dahneke, B.E., Wiley Inc., (1983).

Morgan et al., "The N-terminal End of the C\\\subscript:H\\\2 Domain of Chimeric Human IgG1 anti-HLA-DR is Necessary for Clq, FcγRI and FcγRIII Binding" Immunology 86:319-324 (1995).

Morrison et al., "Chimeric human antibody molecules: Mouse antigen-binding domains with human constant region domains" P Natl Acad Sci USA 81:6851-6855 (Nov. 1984).

Shields et al., "High resolution mapping of the binding site on human IgG1 for FcγRI, FcγRII, FcγRIII, and FcRn and design of IgG1 varients with improved binding to the FcγR" J Biol Chem 276(9):6591-6604 (Mar. 2, 2001).

Tuaillon et al., "Human immunoglobin heavy-chain minilocus recombination in transgenic mice: Gene-segment use in u and γ transcripts" P Natl Acad Sci USA 90:3720-3724 (Apr. 1993).

Vajdos et al., "Comprehensive functional maps of the antigen-binding site of an anti-ErbB2 antibody obtained with shotgyun scanning mutagenesis" J Mol Biol 320:415-428 (2002).

Wang et al., "Potential aggregation prone regions in biotherapeutics" mAbs 1(3):254-267 (May 2009).

Written Opinion of the International Searching Authority for PCT/EP2010/070063, 6 pages.

Wu et al., "Humanization of a Murine Monoclonal Antibody by Simultaneous Optimization of Framework and CDR Residues" J Mol Biol 294:151-162 (1999).

* cited by examiner

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Misc-feature
<222> LOCATION: 1-4, 7, 9
<223> OTHER INFORMATION: Xaa denotes any amino acid residue except Ser
``` and Thr

<400> SEQUENCE: 1

Xaa Xaa Xaa Xaa Thr Thr Xaa Thr Xaa Ser Ser
 1               5                  10

<210> SEQ ID NO 2
<211> LENGTH: 11
<212> TYPE: PRT
<213> ORGANISM: Homo sapiens

<400> SEQUENCE: 2

Trp Gly Gln Gly Thr Leu Val Thr Val Ser Ser
 1               5                  10

<210> SEQ ID NO 3
<211> LENGTH: 11
<212> TYPE: PRT
<213> ORGANISM: Homo sapiens

<400> SEQUENCE: 3

Trp Gly Arg Gly Thr Leu Val Thr Val Ser Ser
 1               5                  10

<210> SEQ ID NO 4
<211> LENGTH: 11
<212> TYPE: PRT
<213> ORGANISM: Homo sapiens

<400> SEQUENCE: 4

Trp Gly Gln Gly Thr Met Val Thr Val Ser Ser
 1               5                  10

<210> SEQ ID NO 5
<211> LENGTH: 11
<212> TYPE: PRT
<213> ORGANISM: Homo sapiens

<400> SEQUENCE: 5

Trp Gly Gln Gly Thr Thr Val Thr Val Ser Ser
 1               5                  10

<210> SEQ ID NO 6
<211> LENGTH: 11
<212> TYPE: PRT
<213> ORGANISM: Homo sapiens

<400> SEQUENCE: 6

Trp Gly Lys Gly Thr Thr Val Thr Val Ser Ser
 1               5                  10

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys
                20                  25                  30

Asp Tyr Phe Pro Glu Pro Val Thr Val Ser Trp Asn Ser Gly Ala
                35                  40                  45

Leu Thr Ser Gly Val His Thr Phe Pro Ala Val Leu Gln Ser Ser
            50                  55                  60

Gly Leu Tyr Ser Leu Ser Ser Val Val Thr Val Pro Ser Ser Ser
            65                  70                  75

Leu Gly Thr Gln Thr Tyr Ile Cys Asn Val Asn His Lys Pro Ser
            80                  85                  90

Asn Thr Lys Val Asp Lys Lys Val Glu Pro Lys Ser Cys Asp Lys
            95                 100                 105

Thr His Thr Cys Pro Pro Cys Pro Ala Pro Glu Leu Leu Gly Gly
           110                 115                 120

Pro Ser Val Phe Leu Phe Pro Pro Lys Pro Lys Asp Thr Leu Met
           125                 130                 135

Ile Ser Arg Thr Pro Glu Val Thr Cys Val Val Val Asp Val Ser
           140                 145                 150

His Glu Asp Pro Glu Val Lys Phe Asn Trp Tyr Val Asp Gly Val
           155                 160                 165

Glu Val His Asn Ala Lys Thr Lys Pro Arg Glu Glu Gln Tyr Asn
           170                 175                 180

Ser Thr Tyr Arg Val Val Ser Val Leu Thr Val Leu His Gln Asp
           185                 190                 195

Trp Leu Asn Gly Lys Glu Tyr Lys Cys Lys Val Ser Asn Lys Ala
           200                 205                 210

Leu Pro Ala Pro Ile Glu Lys Thr Ile Ser Lys Ala Lys Gly Gln
           215                 220                 225

Pro Arg Glu Pro Gln Val Tyr Thr Leu Pro Pro Ser Arg Asp Glu
           230                 235                 240

Leu Thr Lys Asn Gln Val Ser Leu Thr Cys Leu Val Lys Gly Phe
           245                 250                 255

Tyr Pro Ser Asp Ile Ala Val Glu Trp Glu Ser Asn Gly Gln Pro
           260                 265                 270

Glu Asn Asn Tyr Lys Thr Thr Pro Pro Val Leu Asp Ser Asp Gly
           275                 280                 285

Ser Phe Phe Leu Tyr Ser Lys Leu Thr Val Asp Lys Ser Arg Trp
           290                 295                 300

Gln Gln Gly Asn Val Phe Ser Cys Ser Val Met His Glu Ala Leu
           305                 310                 315

His Asn His Tyr Thr Gln Lys Ser Leu Ser Leu Ser Pro Gly Lys
           320                 325                 330

<210> SEQ ID NO 8
<211> LENGTH: 327
<212> TYPE: PRT
<213> ORGANISM: Homo sapiens

<400> SEQUENCE: 8

Ala Ser Thr Lys Gly Pro Ser Val Phe Pro Leu Ala Pro Cys Ser
 1               5                  10                  15

Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala
            35                  40                  45

Leu Thr Ser Gly Val His Thr Phe Pro Ala Val Leu Gln Ser Ser
            50                  55                  60

Gly Leu Tyr Ser Leu Ser Ser Val Val Thr Val Pro Ser Ser Ser
            65                  70                  75

```
Leu Gly Thr Lys Thr Tyr Thr Cys Asn Val Asp His Lys Pro Ser
            80                  85                  90

Asn Thr Lys Val Asp Lys Arg Val Glu Ser Lys Tyr Gly Pro Pro
            95                  100                 105

Cys Pro Ser Cys Pro Ala Pro Glu Phe Leu Gly Gly Pro Ser Val
            110                 115                 120

Phe Leu Phe Pro Pro Lys Pro Lys Asp Thr Leu Met Ile Ser Arg
            125                 130                 135

Thr Pro Glu Val Thr Cys Val Val Val Asp Val Ser Gln Glu Asp
            140                 145                 150

Pro Glu Val Gln Phe Asn Trp Tyr Val Asp Gly Val Glu Val His
            155                 160                 165

Asn Ala Lys Thr Lys Pro Arg Glu Glu Gln Phe Asn Ser Thr Tyr
            170                 175                 180

Arg Val Val Ser Val Leu Thr Val Leu His Gln Asp Trp Leu Asn
            185                 190                 195

Gly Lys Glu Tyr Lys Cys Lys Val Ser Asn Lys Gly Leu Pro Ser
            200                 205                 210

Ser Ile Glu Lys Thr Ile Ser Lys Ala Lys Gly Gln Pro Arg Glu
            215                 220                 225

Pro Gln Val Tyr Thr Leu Pro Pro Ser Gln Glu Glu Met Thr Lys
            230                 235                 240

Asn Gln Val Ser Leu Thr Cys Leu Val Lys Gly Phe Tyr Pro Ser
            245                 250                 255

Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Glu Gly
            290                 295                 300

Asn Val Phe Ser Cys Ser Val Met His Glu Ala Leu His Asn His
            305                 310                 315

Tyr Thr Gln Lys Ser Leu Ser Leu Ser Leu Gly Lys
            320                 325

<210> SEQ ID NO 9
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Misc-feature
<222> LOCATION: 1-11
<223> OTHER INFORMATION: Humanized anti IL13Ra1 antibody FR4 region

<400> SEQUENCE: 9

Trp Gly Gln Gly Thr Leu Val Ile Val Ser Ser
  1               5                  10

<210> SEQ ID NO 10
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Misc-feature
<222> LOCATION: 1-11
```

```
<223> OTHER INFORMATION: Humanized anti OX40L antibody FR4 region

<400> SEQUENCE: 10

Trp Gly Gln Gly Ala Leu Val Thr Val Ser Ser
 1               5                  10

<210> SEQ ID NO 11
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Misc-feature
<222> LOCATION: 1-4, 7, 9
<223> OTHER INFORMATION: Xaa denotes any amino acid residue except Ser
      and Thr
<220> FEATURE:
<221> NAME/KEY: Misc-feature
<222> LOCATION: 6
<223> OTHER INFORMATION: Xaa denotes Thr
<220> FEATURE:
<221> NAME/KEY: Misc-feature
<222> LOCATION: 10-11
<223> OTHER INFORMATION: Xaa denotes Ser

<400> SEQUENCE: 11

Xaa Xaa Xaa Xaa Thr Xaa Xaa Thr Xaa Xaa Xaa
 1               5                  10
```

SEQUENCE DEPENDENT AGGREGATION

CROSS-REFERENCE TO RELATED APPLICATIONS

This application is a divisional application of U.S. application Ser. No. 13/515,428 filed on Jun. 12, 2012, pending, which is an application made under 35 US § 371 based on International Application No. PCT/EP2010/070063 filed on Dec. 17, 2010, and claims the benefit of priority of European patent application number 09015832.0, filed on Dec. 22, 2009, the contents of both of which are incorporated herein by reference in their entirety.

Herein is reported a method for reducing immunoglobulin aggregation in concentrated solutions by reverting one or two mutation(s) in the fourth framework region, i.e. in the J-element, of an immunoglobulin heavy chain to the hydrophilic or natural germline amino acid residue.

BACKGROUND OF THE INVENTION

Due to their chemical and physical properties, such as molecular weight and domain architecture including secondary modifications, the downstream processing of immunoglobulins is very complicated. Concentrated immunoglobulin solutions are required not only for formulated drugs but also for intermediates in downstream processing (DSP) to achieve low volumes for economic handling and application storage.

Also the final formulation of the immunoglobulin requires a highly concentrated solution. For example, for subcutaneous application immunoglobulin concentrations of more than 100 mg/ml, i.e. about 150 mg/ml, are required. But at least some immunoglobulins tend to aggregate at unphysiologically high concentrations of 100 mg/ml or more.

In WO 2009/000098 a sequence based engineering and optimization of single chain antibodies is reported.

SUMMARY OF THE INVENTION

Herein is reported a method for reducing immunoglobulin aggregation in a concentrated solution. It has been found that two or even a single reverting mutation in the fourth framework region of an immunoglobulin heavy chain can reduce the formation of aggregates allowing the provision of a highly concentrated solution of the reverted immunoglobulin variant with reduced aggregate content. Therefore, herein are reported as individual aspects a method for reducing the aggregation of an immunoglobulin in solution, a method for modifying an immunoglobulin, a method for producing an immunoglobulin, and a method for humanizing an immunoglobulin.

All the methods as reported herein comprise the following steps:
  a) aligning the amino acid sequence of the fourth heavy chain framework region of an immunoglobulin with a reference amino acid sequence to achieve maximal level of amino acid sequence identity,
  b) identifying aligned amino acid sequence positions with different amino acid residues in the fourth heavy chain framework region amino acid sequence of the immunoglobulin and of the reference amino acid sequence,
  c) modifying the immunoglobulin amino acid sequence by substituting an or at least one amino acid residue in the fourth heavy chain framework region amino acid sequence of the immunoglobulin at a position identified in b) for the respective threonine or serine residue as present in the reference amino acid sequence, whereby at the substituted position the amino acid residue is threonine or serine in the reference amino acid sequence, and whereby the amino acid residue is not threonine and not serine in the fourth heavy chain framework region amino acid sequence of the immunoglobulin,
  d) optionally providing a nucleic acid sequence encoding the modified immunoglobulin amino acid sequence.

In one embodiment only the difference of threonine residues is determined and changed. In another embodiment the reference amino acid sequence to the fourth framework region of the immunoglobulin is the amino acid sequence xxxxTTxTxSS (SEQ ID NO: 01) with x denoting any amino acid residue except threonine and serine. In a further embodiment the reference amino acid sequence is the amino acid sequence xxxxTxxTxxx (SEQ ID NO: 11) with x at positions 1, 2, 3, 4, 7 and 9 denoting any amino acid residue except threonine and serine and x at position 6 denoting threonine and x at position 10 and 11 denoting serine, whereby the difference of threonine residues at position 5 and/or 8 in the reference amino acid sequence to the amino acid sequence of the fourth framework region of the immunoglobulin heavy chain is identified in step b) and modified in step c). In one embodiment the reference amino acid sequence is a human germline amino acid sequence. In one embodiment of all aspects as reported herein the methods comprise the following steps:
  a) aligning the amino acid sequence of the fourth heavy chain framework region of the immunoglobulin with the amino acid sequence WGQGTLVTVSS (SEQ ID NO: 02), or the amino acid sequence WGRGTLVTVSS (SEQ ID NO: 03), or the amino acid sequence WGQGTMVTVSS (SEQ ID NO: 04), or the amino acid sequence WGQGTTVTVSS (SEQ ID NO: 05), or the amino acid sequence WGKGTTVTVSS (SEQ ID NO: 06) to achieve maximal level of amino acid sequence identity,
  b) identifying aligned amino acid positions with different amino acid residues in the fourth heavy chain framework region amino acid sequence of the immunoglobulin and the reference amino acid sequence,
  c) modifying the immunoglobulin by substituting an amino acid residue in the fourth heavy chain framework region amino acid sequence at a position identified in b) for the respective threonine or serine residue present in the reference amino acid sequence, whereby the amino acid residue at the position is threonine or serine in the reference amino acid sequence and whereby the amino acid residue at the position is not threonine and not serine in the fourth heavy chain framework region amino acid sequence of the immunoglobulin,
  d) optionally providing a nucleic acid sequence encoding the modified immunoglobulin amino acid sequence.

In one embodiment of the aspects as reported herein the methods comprise as first step the step of providing or determining the amino acid sequence of the fourth framework region of the immunoglobulin heavy chain. In one embodiment the reference sequence is the amino acid sequence WGQGTLVTVSS (SEQ ID NO: 02). In another embodiment the reference amino acid sequence is xxxxTxxTxxx (SEQ ID NO: 11). In one embodiment the difference of the threonine residues at position 5 or/and 8 of the reference amino acid sequence is determined. In one embodiment only the difference of threonine residues is determined and changed.

In one aspect as reported herein the method is a method for producing an immunoglobulin comprising the following steps:
- a) aligning the amino acid sequence of the fourth heavy chain framework region of the immunoglobulin with the reference amino acid sequence xxxxTTxTxSS (SEQ ID NO: 01) or xxxxTxxTxxx (SEQ ID NO: 11) to achieve maximal level of amino acid sequence identity,
- b) identifying aligned amino acid sequence positions with different amino acid residues at position 5 and/or 6 and/or 8 and/or 10 and/or 11 in the fourth heavy chain framework region amino acid sequence of the immunoglobulin and the reference amino acid sequence,
- c) modifying the fourth heavy chain framework region amino acid sequence of the immunoglobulin by substituting an amino acid residue in the fourth heavy chain framework region amino acid sequence at a position identified in b) for the respective threonine or serine residue as in the reference amino acid sequence, whereby the amino acid residue at the position is threonine or serine in the reference amino acid sequence, and whereby the amino acid residue at the position is not threonine and not serine in the fourth heavy chain framework region amino acid sequence of the immunoglobulin,
- d) cultivating a mammalian cell comprising the nucleic acid encoding the modified immunoglobulin heavy chain amino acid sequence and a nucleic acid encoding a corresponding light chain amino acid sequence for the expression of the immunoglobulin heavy and light chain,
- e) recovering the immunoglobulin from the mammalian cell or the cultivation medium and thereby producing an immunoglobulin.

In one embodiment the reference amino acid sequence is the amino acid sequence WGQGTLVTVSS (SEQ ID NO: 02), or the amino acid sequence WGRGTLVTVSS (SEQ ID NO: 03), or the amino acid sequence WGQGTMVTVSS (SEQ ID NO: 04), or the amino acid sequence WGQGTTVTVSS (SEQ ID NO: 05), or the amino acid sequence WGKGTTVTVSS (SEQ ID NO: 06). In one embodiment the step of modifying the fourth heavy chain framework region amino acid sequence of the immunoglobulin is substituting an amino acid residue in the fourth heavy chain framework region amino acid sequence at a position identified in b), which is threonine in the reference amino acid sequence and which is not threonine in the fourth heavy chain framework region amino acid sequence, for the respective threonine residue as present in the reference amino acid sequence. In another embodiment the modifying is of at least one position identified. In one embodiment the reference amino acid sequence is the amino acid sequence WGQGTLVTVSS (SEQ ID NO: 02). In one embodiment the immunoglobulin is a human or humanized immunoglobulin. In another embodiment the mammalian cell is a CHO cell or a HEK cell. In another embodiment the difference of the threonine residues at position 5 and/or 8 of the reference amino acid sequence is determined.

Another aspect as reported herein is a method for humanizing an immunoglobulin comprising the following steps:
- a) aligning the amino acid sequence of the fourth heavy chain framework region of the immunoglobulin with the reference amino acid sequence xxxxTTxTxSS (SEQ ID NO: 01) or xxxxTxxTxxx (SEQ ID NO: 11) to achieve maximal level of amino acid sequence identity,
- b) identifying aligned amino acid sequence positions with different amino acid residues in the fourth heavy chain framework region amino acid sequence of the immunoglobulin and the reference amino acid sequence,
- c) humanizing the immunoglobulin by substituting an amino acid residue in the fourth heavy chain framework region amino acid sequence at a position identified in b) for the respective threonine or serine residue as in the reference sequence, whereby the amino acid residue at the position is threonine or serine in the reference amino acid sequence, and whereby the amino acid residue at the position is not threonine and not serine in the fourth heavy chain framework region amino acid sequence of the immunoglobulin,
- d) optionally providing a nucleic acid sequence encoding the humanized immunoglobulin.

DETAILED DESCRIPTION OF THE INVENTION

It has been found that the exchange of two or even a single threonine and/or serine amino acid residue to a small hydrophobic or non-polar amino acid residue, such as isoleucine or alanine, in the amino acid sequence of the fourth immunoglobulin heavy chain framework region increases the tendency of the immunoglobulin to form aggregates in solution, especially in solutions with high salt concentration and/or high immunoglobulin concentration. By reverting the exchanged amino acid residues back to the naturally occurring threonine and/or serine residue(s) the tendency to form aggregates in solution, especially in concentrated solutions, is distinctly reduced.

In one aspect the method as reported herein is a method for reducing the aggregation of an immunoglobulin in solution comprising the following steps:
- determining whether one or more threonine and/or serine residues in the fourth framework region amino acid sequence of the heavy chain of the immunoglobulin have been changed by comparing the amino acid sequence with a reference amino acid sequence for the fourth framework region amino acid sequence,
- reverting the amino acid sequence of the immunoglobulin by modifying at least one of the exchanged threonine and/or serine residues back to the reference threonine and/or serine residue and thereby reducing the aggregation of an immunoglobulin in solution.

The term "aligning" stands for the process of lining up two or more amino acid sequences to achieve maximal level of amino acid sequence identity and conservation. It comprises the determination of positional homology for molecular sequences, involving the juxtaposition of amino acids or nucleotides in homologous molecules. As a result the compared sequences are presented in a form that the regions of greatest statistical similarity are shown.

"Maximal level of amino acid sequence identity" with respect to a reference amino acid sequence is defined as the percentage of amino acid residues in a candidate amino acid sequence that are identical with the amino acid residues in the reference amino acid sequence, after aligning the sequences and introducing gaps, if necessary, to achieve the maximum percent sequence identity, and not considering any conservative substitutions as part of the sequence identity. Alignment for purposes of determining amino acid sequence identity can be achieved in various ways, for instance, using publicly available computer software such as BLAST, BLAST-2, ALIGN or Megalign (DNASTAR) software. Those skilled in the art can determine appropriate parameters for aligning amino acid sequences, including any algorithms needed to achieve maximal alignment over the full length of the amino acid sequences being compared. For purposes herein, however, "% amino acid sequence identity" values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In a further aspect the method as reported herein is a method for modifying an immunoglobulin comprising the following steps:
  determining whether one or more threonine and/or serine residues in the fourth framework region amino acid sequence of the heavy chain of the immunoglobulin have been changed by comparing the amino acid sequence with a reference amino acid sequence for the fourth framework region amino acid sequence,
  reverting the amino acid sequence of the immunoglobulin by modifying at least one of the exchanged threonine and/or serine residues back to the reference threonine and/or serine residue and thereby modifying an immunoglobulin.

In one aspect the method as reported herein is a method for humanizing an immunoglobulin comprising the following steps:
  determining by comparing the amino acid sequence of the fourth framework region of the heavy chain of a chimeric immunoglobulin, a CDR-grafted immunoglobulin, a T-cell epitope reduced or depleted immunoglobulin, or a variant thereof with a reference amino acid sequence for the fourth framework region whether one or more threonine and/or serine residues have been replaced by a different amino acid residue,
  reverting the amino acid sequence of the immunoglobulin by modifying at least one of the exchanged threonine and/or serine residues back to the threonine and/or serine residue as in the reference amino acid sequence and thereby humanizing an immunoglobulin.

The term "fourth framework region amino acid sequence" denotes the amino acid sequence of the fourth framework region of the heavy chain of an immunoglobulin. This amino acid sequence starts with the amino acid residue directly C-terminal to the complementarity determining region 3 (CDR 3) of the immunoglobulin heavy chain and ends with the last amino acid residue of the heavy chain variable domain. In one embodiment the amino acid residues of the CDR 3 of the immunoglobulin heavy chain are determined according to Kabat.

The term "chimeric immunoglobulin" denotes an immunoglobulin comprising amino acid residues derived from an immunoglobulin of a first species and amino acid residues derived from a second species not identical with the first species. If the acceptor species is human then the chimeric immunoglobulin is a "humanized immunoglobulin". For the most part, a humanized immunoglobulin is derived from a human immunoglobulin (recipient or acceptor immunoglobulin), in which the amino acid sequence of one or more hypervariable region(s) determined according to Kabat and/or Chothia and/or other numbering systems are changed to the amino acid sequence of a hypervariable region of a non-human species (donor immunoglobulin). A humanized immunoglobulin in which the entire hypervariable regions according to Kabat and/or Chothia and/or other numbering systems of a human acceptor immunoglobulin are replaced by the corresponding amino acid residues of a non-human donor immunoglobulin are denoted as "CDR-grafted immunoglobulin". Exemplary non-human donor immunoglobulins are mouse, rat, rabbit, dog, hamster, sheep, or non-human primate immunoglobulins, having the desired specificity and affinity towards an antigen of interest (see e.g. Morrison, S. L., et al., Proc. Natl. Acad. Sci. USA 81 (1984) 6851-6855; U.S. Pat. No. 5,202,238; U.S. Pat. No. 5,204,244). In some instances, framework region (FR) residues of the human immunoglobulin are replaced by corresponding non-human residues. Furthermore, humanized immunoglobulins may comprise further modifications, e.g. amino acid residues that are not found in the acceptor immunoglobulin or in the donor immunoglobulin. Such modifications result in variants of such recipient or donor immunoglobulin, which are homologous but not identical to the corresponding parent sequence. A humanized immunoglobulin optionally will also comprise at least a portion of an immunoglobulin constant region, typically that of a human immunoglobulin.

In one embodiment the immunoglobulin is a chimeric immunoglobulin, or a CDR-grafted immunoglobulin, or a T-cell epitope reduced or depleted immunoglobulin, or a variant thereof. In one embodiment the immunoglobulin comprises a human heavy chain constant region or a variant thereof. In a further embodiment the human constant region is of IgG1 subclass, or of IgG4 subclass, or of IgG2 subclass, or of IgG3 subclass, or of SEQ ID NO: 07, or SEQ ID NO: 08, or is a variant thereof.

In one embodiment the constant region is modified in such a way that no Fcγ receptor (e.g. FcγRIIIa) binding and/or no C1q binding as defined below can be detected. In one embodiment the constant region is a human constant region and is either of human IgG4 subclass or is a mutated Fc part from human IgG1 subclass. In another embodiment the constant region is of human IgG1 subclass comprising the mutations L234A and L235A (positions determined according to full length, i.e. including the variable domain, human IgG1 heavy chain amino acid sequence). While IgG4 shows reduced Fcγ receptor (FcγRIIIa) binding, immunoglobulins of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment the constant region is in regard to Fcγ receptor binding of IgG4 subclass or of IgG1 or IgG2 subclass, with a mutation in L234, L235, and/or D265, and/or contains the PVA236 mutation. In one embodiment the mutation is S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). In a further embodiment the mutation is S228P of IgG4, and L234A and L235A of IgG1. The constant region of an immunoglobulin is directly involved in ADCC (antibody-dependent cell-mediated cytotoxicity) and CDC (complement-dependent cytotoxicity). An immunoglobulin which does not bind Fcγ receptor and/or complement factor C1q does not elicit antibody-dependent cellular cytotoxicity (ADCC) and/or complement dependent cytotoxicity (CDC).

The term "T-cell epitope depleted immunoglobulin" denotes an immunoglobulin which was modified to remove or reduce immunogenicity by removing human T-cell epitopes (peptide sequences within proteins with the capacity to bind to MHC Class II molecules). By this method interactions between amino acid side chains of the peptide and specific binding pockets with the MHC class II binding groove are identified. The identified immunogenic regions are changed to eliminate immunogenicity. Such methods are described in general in, e.g., WO 98/52976 or in WO 98/08097.

The term "variant thereof" denotes an immunoglobulin comprising conservative sequence modifications or an altered glycosylation pattern. The term "conservative sequence modifications" denotes amino acid substitutions including the ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), non-polar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine). Another type of variant of the immunoglobulin alters the original glycosylation pattern of the immunoglobulin. By altering is meant deleting one or more glycosylation sites found in the immunoglobulin, and/or introducing one or more glycosylation sites that are not present in the immunoglobulin. Glycosylation of immunoglobulins is typically N-linked. N-linked refers to the attachment of the carbohydrate moiety to the side chain of an asparagine residue. The tripeptide sequences asparagine-X-serine and asparagine-X-threonine and asparagine-X-cysteine, where X can be any amino acid, are the recognition sequences for enzymatic attachment of the carbohydrate moiety to the asparagine side chain.

In one embodiment the reference sequence is the sequence of SEQ ID NO: 02 to 06, or the sequence of SEQ ID NO: 01, or the sequence of SEQ ID NO: 11. In another embodiment the determining and reverting is of the replaced threonine residues.

The invention is in the following exemplified with an anti-IL13Rα1 antibody and an anti-OX40L antibody. The corresponding amino acid sequences and production methods are reported in WO 2006/072564 and WO 2006/029879 (which are incorporated herein by reference). These antibodies are only used to illustrate the aspects as reported herein and not to present any limitation. The scope of the invention is set forth in the appended set of claims.

The anti-IL13Rα1 antibody is in the following denoted as parent antibody and has an amino acid sequence of the fourth heavy chain framework region of WGQGTLVIVSS (SEQ ID NO: 09). The comparison with the amino acid sequence of SEQ ID NO: 01 and SEQ ID NO: 11 is shown below.

```
          1
1         0
xxxxTTxTxSS,         (SEQ ID NO: 01)
or xxxxTxxTxxx          (SEQ ID NO: 11)
to

WGQGTLVIVSS          (SEQ ID NO: 09)
```

It can be seen that one difference between the amino acid sequences is an isoleucine residue at the 8$^{th}$ position of SEQ ID NO: 09 instead of the threonine residue in SEQ ID NO: 01 or SEQ ID NO: 11. Therefore, a variant antibody has been produced in which the isoleucine residue is reverted back to a threonine residue.

Whereas the parent antibody shows high levels of aggregate formation the reverted variant antibody has a clearly reduced tendency to form aggregates. In FIG. 1 the rates of the size increase (nm/h) of aggregates of the parent anti-IL13Rα1 antibody at an antibody concentration of 30 mg/ml at 50° C. and varying ionic strength is shown. Also shown in FIG. 1 are the rates obtained with a variant anti-IL13Rα1 antibody in which the isoleucine residue at amino acid position 115 (corresponding to the 8th position in SEQ ID NO: 01, 11 and 09) in the fourth framework region of the heavy chain amino acid sequence has been reverted to threonine as single and sole difference to the parent anti-IL13Rα1 antibody. The single reverting mutation reduces the rate of aggregate size increase at all examined ionic strengths.

In FIG. 2 the analytical size exclusion chromatograms of two samples stored for 9 weeks at 40° C. in the same formulation is shown. The respective data is listed in the following Table 1.

TABLE 1

Analytical data of samples stored for 9 weeks at 40° C.

| | relative area monomer [%] | relative area low molecular weight compounds [%] | relative area high molecular weight compounds [%] | relative increase HMWs [%] |
|---|---|---|---|---|
| parent anti-IL13Rα1 antibody stored at −80° C. (reference value) | 98.6 | 0.04 | 1.4 | — |
| parent anti-IL13Rα1 antibody stored at 40° C. for 9 weeks | 93.7 | 4.2 | 2.0 | 48.9 |

TABLE 1-continued

Analytical data of samples stored for 9 weeks at 40° C.

| | relative area monomer [%] | relative area low molecular weight compounds [%] | relative area high molecular weight compounds [%] | relative increase HMWs [%] |
|---|---|---|---|---|
| variant anti-IL13Rα1 antibody stored at −80° C. (reference value) | 97.3 | 0.1 | 2.5 | — |
| variant anti-IL13Rα1 antibody stored at 40° C. for 9 weeks | 93.2 | 3.9 | 2.9 | 13.4 |

It can be seen that the tendency to form aggregates of the reverted variant antibody is reduced by more than 50% compared to the parent antibody.

In FIG. 3 the Kyte-Doolittle plot of the heavy chain residues 1 to 130 with an analysis or averaging window of 9 residues of the parent anti-IL13Rα1 antibody is shown. In the forth framework region the plot shows the highest hydrophobicity values for the entire heavy chain. In FIG. 4 the Kyte-Doolittle plot of the heavy chain of the variant anti-IL13Rα1 antibody is shown. It can be seen that the hydrophobicity values of the fourth framework region are distinctly reduced in the reverted variant antibody.

In FIG. 5 the Kyte-Doolittle plot of the heavy chain residues 1 to 130 with an analysis/averaging window of 9 residues of an anti-OX40L antibody is shown. It can be seen that also in this case the highest hydrophobicity value is in the fourth heavy chain framework region. By analyzing the amino acid sequence of the fourth heavy chain framework region an amino acid exchange can be determined as shown below.

```
         1
1        0
xxxxTxTxSS,       (SEQ ID NO: 01)
or xxxxTxxTxxx,      (SEQ ID NO: 11)
or WGQGTLVTVSS       (SEQ ID NO: 02)
to

WGQGALVTVSS.      (SEQ ID NO: 10)
```

Reverting this single amino acid change back to the naturally occurring germline threonine residue reduced the hydrophobicity of the antibody as shown in the Kyte-Doolittle plot in FIG. 6.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO: 01 xxxxTTxTxSS—reference amino acid sequence

SEQ ID NO: 02 WGQGTLVTVSS—partial germline FR4/J-element amino acid sequence.

SEQ ID NO: 03 WGRGTLVTVSS—partial germline FR4/J-element amino acid sequence.

SEQ ID NO: 04 WGQGTMVTVSS—partial germline FR4/J-element amino acid sequence.

SEQ ID NO: 05 WGQGTTVTVSS—partial germline FR4/J-element amino acid sequence.

SEQ ID NO: 06 WGKGTTVTVSS—partial germline FR4/J-element amino acid sequence.

SEQ ID NO: 07 human IgG1 heavy chain constant region amino acid sequence.

SEQ ID NO: 08 human IgG4 heavy chain constant region amino acid sequence.

SEQ ID NO: 09 WGQGTLVIVSS—amino acid sequence of an anti-IL13Rα1 antibody.

SEQ ID NO: 10 WGQGALVTVSS—amino acid sequence of an anti-OX40L antibody.

SEQ ID NO: 11 xxxxTxxTxxx—reference amino acid sequence.

MATERIALS AND METHODS

Analytical Size Exclusion Chromatography

Figure 1:
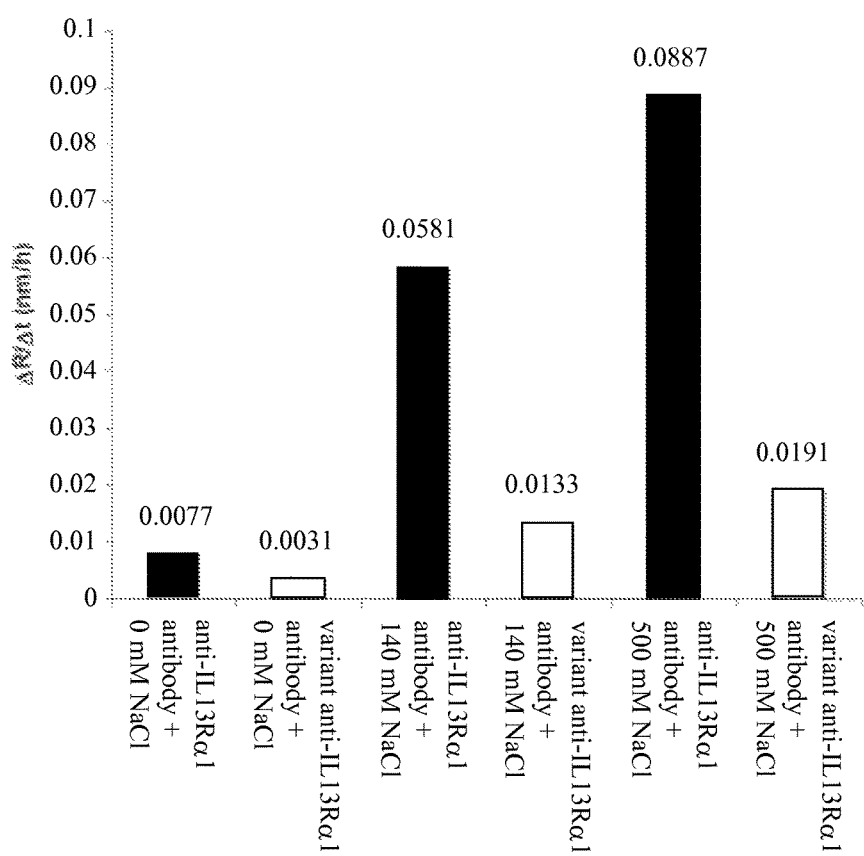
FIG. 1 Rate of particle size increase per time unit in a solution of 30 mg/ml anti-IL13Rα1 antibody (a) and the reverted variant antibody (b) both in 20 mM histidine buffer, pH 6, with 0, 140 and 500 mM NaCl at 50° C., determined by dynamic light scattering.

The content of high molecular weight species (HMWs), antibody monomers and low molecular weight species (LMWs) was determined by analytical size-exclusion chromatography using a TSK 3000S WXL 7.8×300 mm column (Tosoh, Stuttgart, Germany). As eluent, a buffer solution containing 200 mM $KH_2PO_4$ and 250 mM KCl at pH 7.0 was used at a flow rate of 0.5 ml/min. An amount of 150 μg of protein was loaded per run. Detection was accomplished via UV absorption at 280 nm.

Dynamic Light Scattering (DLS)

DLS is a non-invasive technique for measuring particle size, typically in the sub-micron size range. In the current invention the Zetasizer Nano S apparatus (Malvern Instruments, Worcestershire, UK) with a temperature controlled quartz cuvette (25° C.) was used for monitoring a size range between 1 nm and 6 μm. The intensity of the back scattered laser light was detected at an angle of 173°. The intensity fluctuates at a rate that is dependent upon the particle diffusion speed, which in turn is governed by particle size. Particle size data can therefore be generated from an analysis of the fluctuation in scattered light intensity (Dahneke, B. E. (ed), Measurement of Suspended Particles by Quasielectric Light Scattering, Wiley Inc. (1983); Pecora, R., Dynamic Light Scattering: Application of Photon Correlation Spectroscopy, Plenum Press (1985)). The size distribution by intensity was calculated using the multiple narrow mode of the DTS software (Malvern).

Example 1

Production of Variant Anti-IL13Rα1 Antibody

The anti-IL13Rα1 antibody light and heavy chain encoding genes were separately assembled in mammalian cell expression vectors. Thereby the gene segments encoding the anti-IL13Rα1 antibody light chain variable region ($V_L$) and the human κ-light chain constant region ($C_L$) were joined as were gene segments for the anti-IL13Rα1 antibody heavy chain variable region ($V_H$) and the human γ1-heavy chain constant region ($C_{H1}$-Hinge-$C_{H2}$-$C_{H3}$). General information regarding the nucleotide sequences of human light and heavy chains from which the codon usage is given in: Kabat, E. A., Wu, T. T., Perry, H. M., Gottesman, K. S., and Foeller, C. Sequences of Proteins of Immunological Interest, Fifth Ed., NIH Publication No. 91-3242 (1991). The transcription unit of the anti-IL13Rα1 antibody κ-light chain is composed of the following elements:
the immediate early enhancer and promoter from the human cytomegalovirus (HCMV),
a synthetic 5'-UT including a Kozak sequence,
a murine immunoglobulin heavy chain signal sequence including the signal sequence intron,
the cloned anti-IL13Rα1 antibody variable light chain cDNA arranged with a unique BsmI restriction site at the 5' end and a splice donor site and a unique NotI restriction site at the 3' end,
the genomic human κ-gene constant region, including the intron 2 mouse Ig-κ enhancer (Picard, D., and Schaffner, W., Nature 307 (1984) 80-82), and
the human immunoglobulin κ-polyadenylation ("poly A") signal sequence.

The transcription unit of the anti-IL13Rα1 antibody γ1-heavy chain is composed of the following elements:
the immediate early enhancer and promoter from the human cytomegalovirus (HCMV),
a synthetic 5'-UT including a Kozak sequence,
a modified murine immunoglobulin heavy chain signal sequence including the signal sequence intron,
the cloned anti-IL13Rα1 antibody variable heavy chain cDNA arranged with a unique BsmI restriction site at the 5' and a splice donor site and a unique NotI restriction site at the 3' end,
the genomic human γ1-heavy gene constant region, including the mouse Ig μ-enhancer (Neuberger, M. S., EMBO J. 2 (1983) 1373-1378),
the human γ1-immunoglobulin polyadenylation ("poly A") signal sequence.

Besides the anti-IL13Rα1 antibody κ-light chain or γ1-heavy chain expression cassette these plasmids contain
a hygromycin resistance gene,
an origin of replication, oriP, of Epstein-Barr virus (EBV),
an origin of replication from the vector pUC18 which allows replication of this plasmid in E. coli, and
a β-lactamase gene which confers ampicillin resistance in E. coli.

An expression plasmid encoding the variant anti-IL13Rα1 antibody γ1-heavy chain was created by site-directed mutagenesis of the parent antibody expression plasmids using the QuickChange™ Site-Directed mutagenesis Kit (Stratagene). Amino acids are numbered according to EU numbering (Edelman, G. M., et al., Proc. Natl. Acad. Sci. USA 63 (1969) 78-85; Kabat, E. A., Wu, T. T., Perry, H. M., Gottesman, K. S., and Foeller, C., (1991) Sequences of Proteins of Immunological Interest, Fifth Ed., NIH Publication No. 91-3242).

A stably transfected CHO clone produces the variant anti-IL13Rα1 antibody at 130 mg/liter. The downstream processing was conducted by employing three sequential chromatographic steps: Protein A chromatography, cation exchange chromatography and anion exchange chromatography.

Example 2

Determination of the Rate of Aggregate Size Increase Via Dynamic Light Scattering In order to follow aggregation over time, dynamic light scattering (DLS) measurements were conducted at regular time intervals. High salt concentrations stabilize hydrophobic interactions; hence hydrophobicity-related aggregation is expected to be more pronounced at high salt concentrations. The change of average particle size (Z-average radius) was monitored as a metric for protein aggregation (FIG. 1). Samples were dialyzed in buffer containing various amounts of NaCl (20 mM His/His-HCl at pH 6.0+0/140/500 mM NaCl) at a protein concentration of 30 mg/ml. DLS measurements were carried out on a Wyatt DynaPro plate reader in 394-well micro titer plates at a temperature of 50° C.

Example 3

Stability Testing of Variant Anti-IL13Rα1 Antibody

Figure 2:
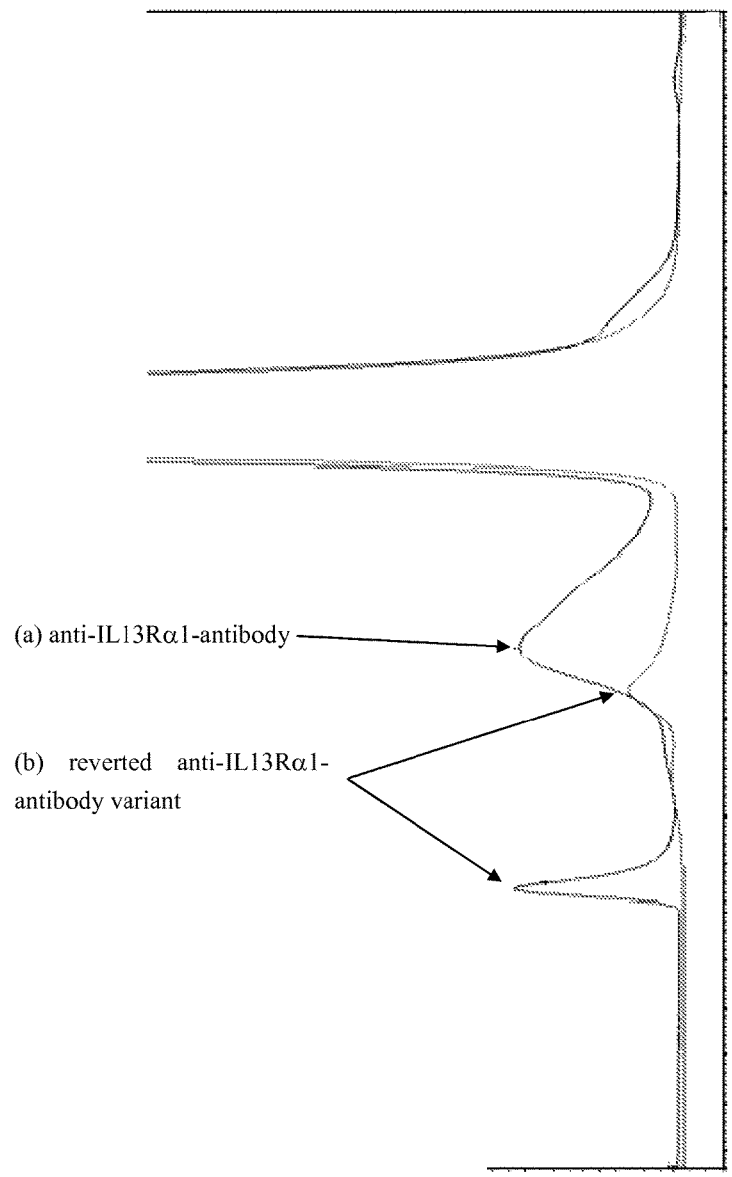
FIG. 2 Analytical size exclusion chromatograms of two solutions of 30 mg/ml anti-IL13Rα1 antibody and the reverted form both in the presence of 500 mM NaCl for 15 h at 10° C.
Figure 3:
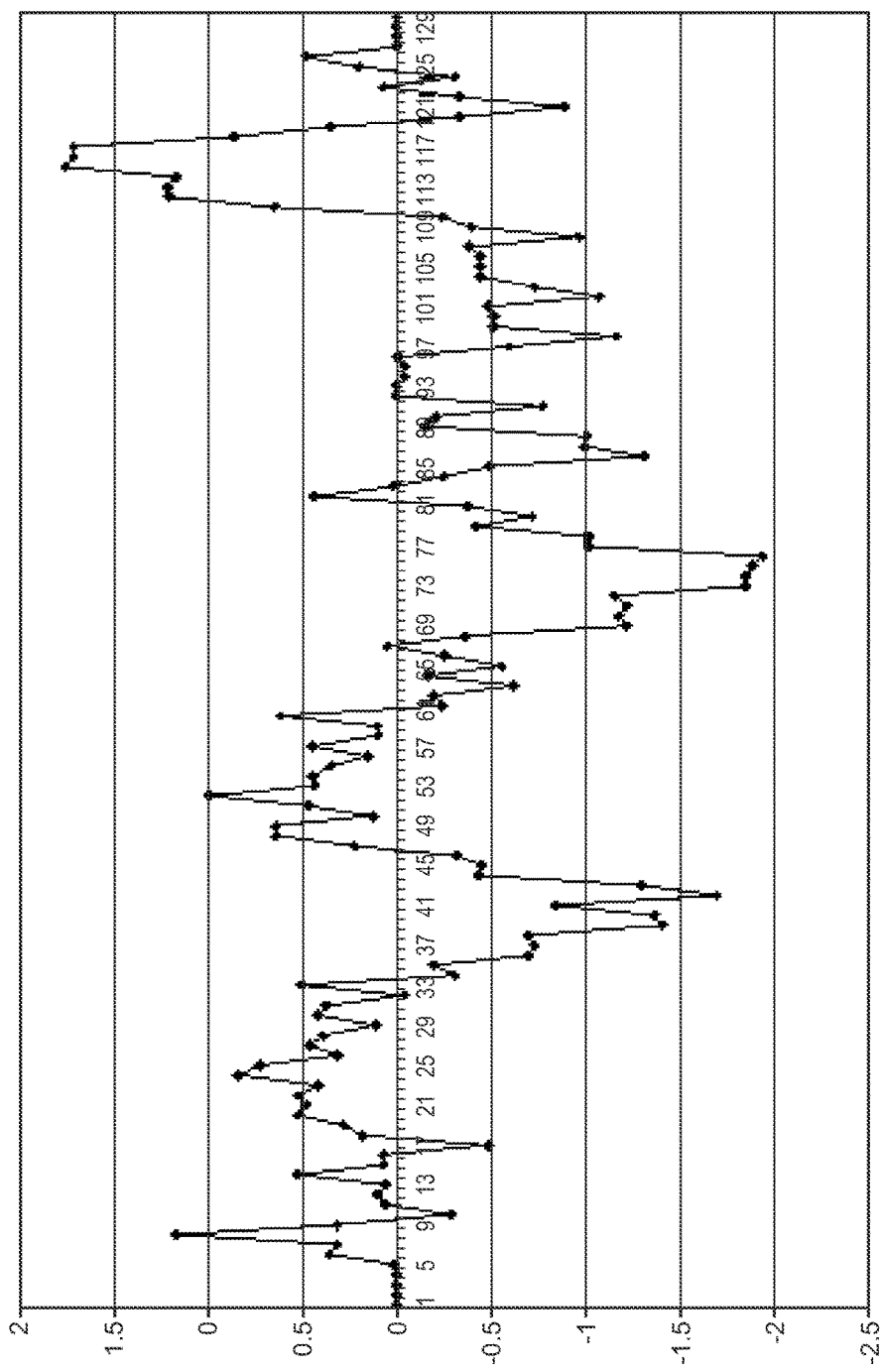
FIG. 3 Kyte-Doolittle plot of the heavy chain residues 1 to 130 with an analysis window of 9 residues of parent anti-IL13Rα1 antibody.
Figure 4:
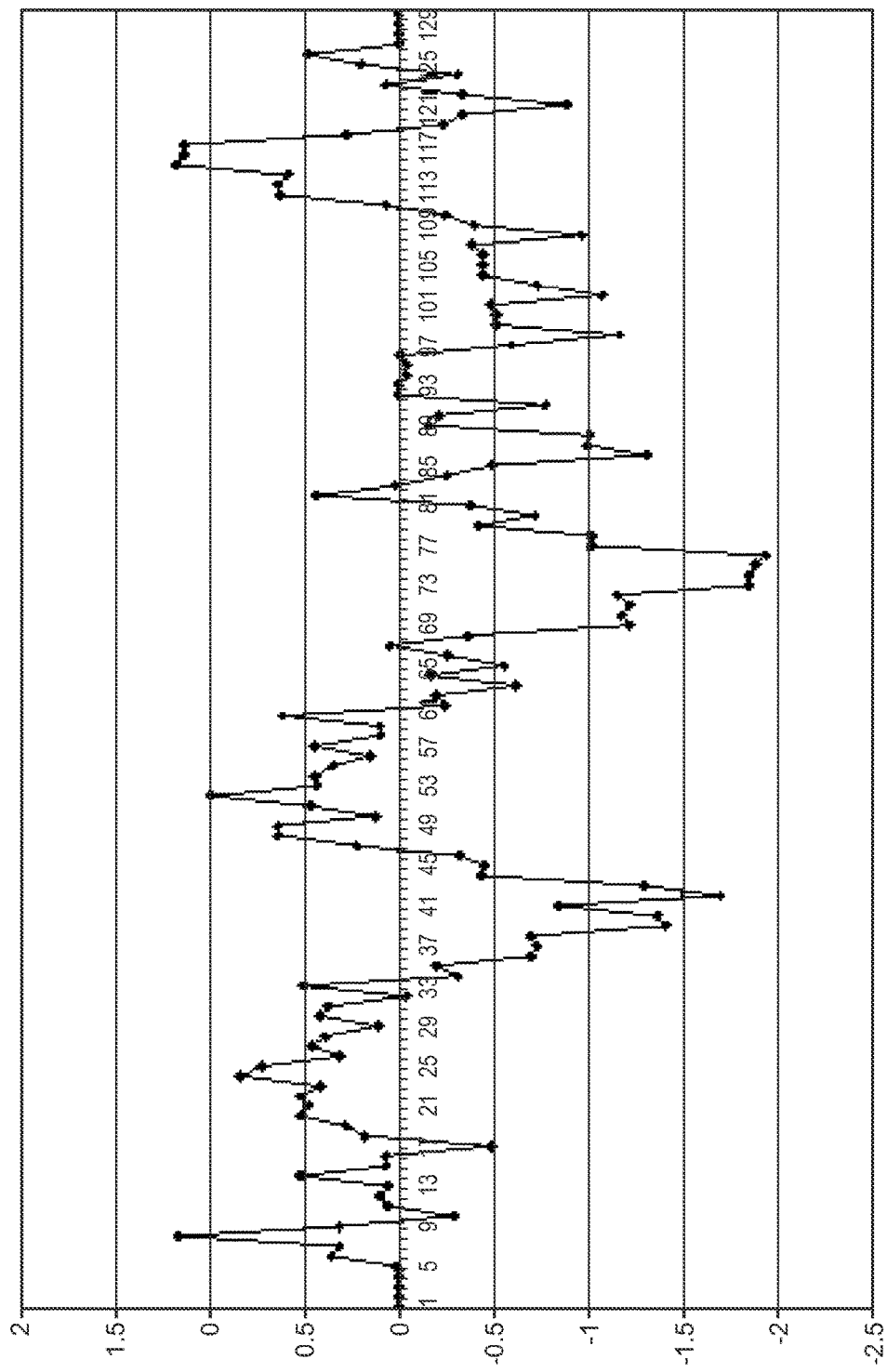
FIG. 4 Kyte-Doolittle plot of the heavy chain residues 1 to 130 with an analysis window of 9 residues of variant anti-IL13Rα1 antibody.
Figure 5:
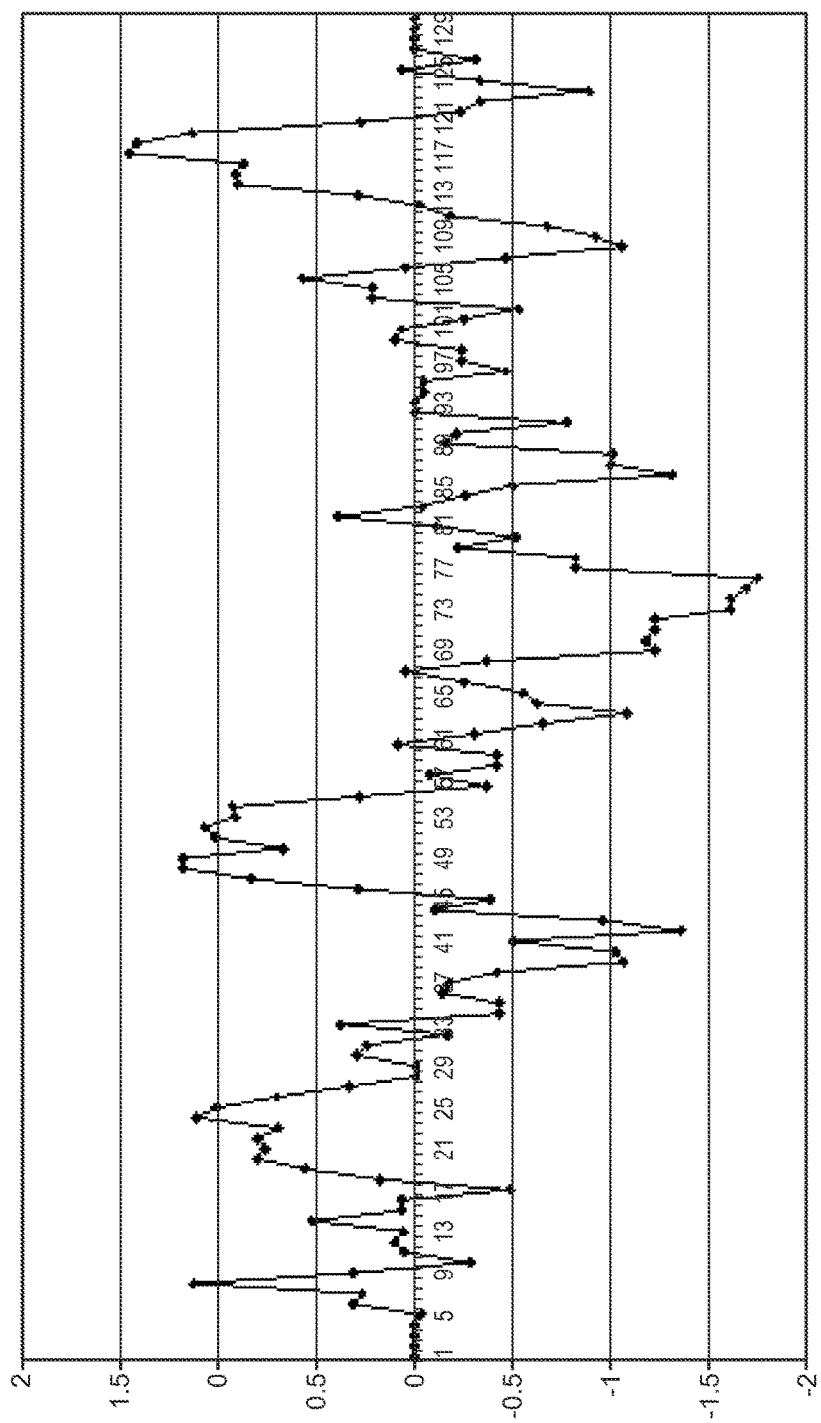
FIG. 5 Kyte-Doolittle plot of the heavy chain residues 1 to 130 with an analysis window of 9 residues of parent anti-OX40L antibody.
Figure 6:
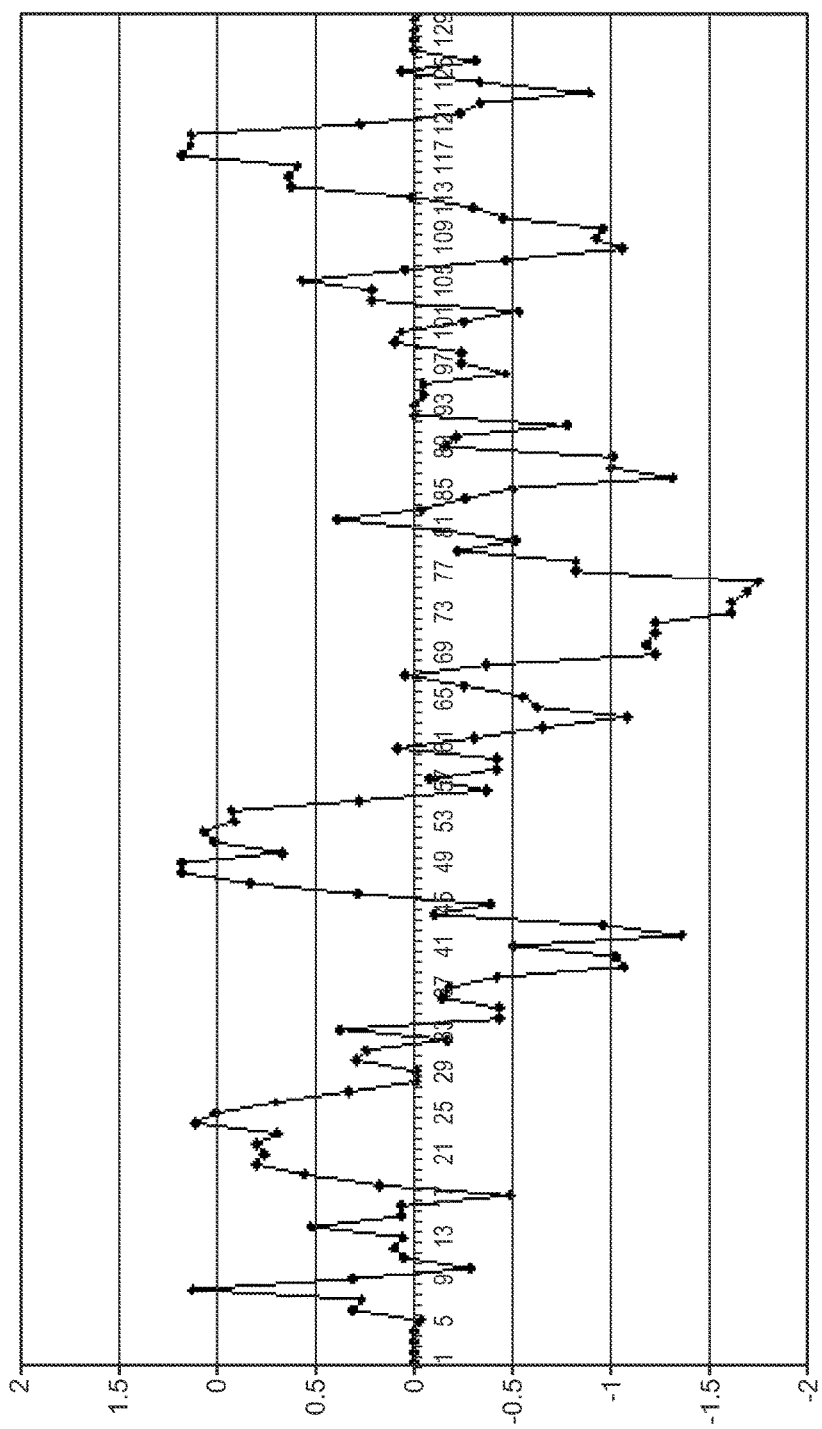
FIG. 6 Kyte-Doolittle plot of the heavy chain residues 1 to 130 with an analysis window of 9 residues of variant anti-OX40L antibody.

Induction of high molecular weight compounds (HMWs) was performed by dialyzing samples in 20 mM His/His-HCl at pH 6.0, containing 0 or 500 mM NaCl, followed by incubation at 10° C. for 15 h. The formation of HMWs compared to the untreated samples was monitored by SEC HPLC (FIG. 2).

The invention claimed is:

1. A method for humanizing the fourth heavy chain framework region of an immunoglobulin comprising the following steps
   a) aligning the amino acid sequence of the fourth heavy chain framework region of the immunoglobulin with a reference sequence, wherein the reference sequence is selected from WGQGTLVTVSS (SEQ ID NO: 02), WGRGTLVTVSS (SEQ ID NO: 03), WGQGTMVTVSS (SEQ ID NO: 04), WGQGTTVTVSS (SEQ ID NO: 05), and WGKGTTVTVSS (SEQ ID NO: 06), to achieve maximal level of amino acid sequence identity,
   b) identifying aligned amino acid positions with a small hydrophobic or non-polar amino acid residue at one or two positions selected from position 5, position 8, and position 5 and position 8, and
   c) humanizing the fourth heavy chain framework region of the immunoglobulin by substituting an amino acid residue in the fourth heavy chain framework region at one or two positions identified in b), which is threonine in the reference sequence and which is not threonine in the fourth heavy chain framework region, for the respective threonine residue as in the reference sequence.

2. The method according to claim 1, wherein the method comprises a further step before the aligning step a) of
   providing or determining the amino acid sequence of the fourth framework region of the immunoglobulin heavy chain.

3. The method according to claim 1, wherein the immunoglobulin is a human or humanized immunoglobulin.

4. The method according to claim 1, wherein the immunoglobulin is a chimeric immunoglobulin or a CDR-grafted immunoglobulin.

5. The method of claim 1 comprising the further step of providing a nucleic acid sequence encoding the humanized immunoglobulin.

* * * * *